(12) United States Patent
Sheftel et al.

(10) Patent No.: US 9,192,761 B2
(45) Date of Patent: Nov. 24, 2015

(54) DEVICE AND METHOD FOR TREATING HYPERHIDROSIS

(71) Applicants: Scott Sheftel, Tucson, AZ (US); Stanley N. Sheftel, Akron, OH (US)

(72) Inventors: Scott Sheftel, Tucson, AZ (US); Stanley N. Sheftel, Akron, OH (US)

(*) Notice: Subject to any disclaimer, the term of this patent is extended or adjusted under 35 U.S.C. 154(b) by 0 days.

(21) Appl. No.: 14/213,735

(22) Filed: Mar. 14, 2014

(65) Prior Publication Data

US 2014/0276357 A1    Sep. 18, 2014

Related U.S. Application Data

(60) Provisional application No. 61/785,674, filed on Mar. 14, 2013.

(51) Int. Cl.
*A61N 1/00* (2006.01)
*A61N 1/32* (2006.01)
*A61F 13/00* (2006.01)

(52) U.S. Cl.
CPC ............ *A61N 1/32* (2013.01); *A61F 13/00063* (2013.01)

(58) Field of Classification Search
CPC ............ D04B 1/14; B32B 15/08; B32B 5/26
USPC ....................... 442/6; 607/108, 112
See application file for complete search history.

(56) References Cited

U.S. PATENT DOCUMENTS

| 4,425,917 | A | * | 1/1984 | Kuznetz | 607/110 |
|---|---|---|---|---|---|
| 5,861,044 | A | * | 1/1999 | Crenshaw | 8/115 |
| 6,602,811 | B1 | * | 8/2003 | Rock et al. | 442/312 |
| 2002/0086036 | A1 | | 7/2002 | Walker | |
| 2005/0010192 | A1 | | 1/2005 | Sun et al. | |
| 2007/0191756 | A1 | | 8/2007 | Tapper | |
| 2010/0209515 | A1 | | 8/2010 | Chantalat et al. | |
| 2012/0064313 | A1 | * | 3/2012 | Rock et al. | 428/212 |

FOREIGN PATENT DOCUMENTS

WO    2010027792 A1    3/2010

OTHER PUBLICATIONS

PCT/US2014/029239—International Search Report and Written Opinion dated Jul. 7, 2014.

* cited by examiner

*Primary Examiner* — Laura Bouchelle
*Assistant Examiner* — Melissa A Snyder
(74) *Attorney, Agent, or Firm* — Hayes Soloway P.C.

(57) ABSTRACT

Device and method for treating hyperhidrosis by application of a fabric including an elemental zinc particle deposition to a treatment area of the skin.

17 Claims, 3 Drawing Sheets

DEVICE AND METHOD FOR TREATING HYPERHIDROSIS

CROSS-REFERENCE TO RELATED APPLICATIONS

This Application claims priority to a U.S. provisional Application filed on Mar. 14, 2013 and having Ser. No. 61/785,674.

FIELD OF THE INVENTION

Embodiments generally relate to device and method for the reduction of sweating and the treatment of hyperhidrosis.

BACKGROUND OF THE INVENTION

Hyperhidrosis is a medical condition in which patients experience excessive sweating. Patients suffering from hyperhidrosis may sweat even when they are resting or the temperature is cool. People naturally sweat when triggered by warm temperatures, exercise, nervousness, fear or anger. However, hyperhidrosis patients sweat excessively without these triggers and appear to have overactive sweat glands. Such uncontrolled sweating can lead to a patient's physical and emotional discomfort.

Current treatments, such as antiperspirants may mask odors from perspiration but fail to prevent sweat release from the skin surface. Other treatment methods including medication, iontophoresis, botulinum toxin injections, or surgery are invasive and may place some patients at risk. Accordingly, it would be an advance in the art to provide a device and method of treating hyperhidrosis that can address substantial arrest of the release of sweat by the skin surface non-invasively and with efficacy.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF PREFERRED EMBODIMENTS

The invention is described in preferred embodiments in the following description with reference to the FIGS., in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," "in certain embodiments," and similar language throughout this specification may, but do not necessarily, all refer to the same embodiment. It is noted that, as used in this description, the singular forms "a," "an" and "the" include plural referents unless the context clearly dictates otherwise.

The described features, structures, or characteristics of the invention(s) may be combined in any suitable manner in one or more embodiments. In the following description, numerous specific details are recited to provide a thorough understanding of embodiments of the invention(s). One skilled in the relevant art will recognize, however, that the invention(s) may be practiced without one or more of the specific details, or with other methods, components, materials, and so forth. In other instances, well-known structures, materials, or operations are not shown or described in detail to avoid obscuring aspects of the invention.

In certain embodiments, Applicants' device for treating hyperhidrosis comprises a fabric and zinc particles disposed on at least a portion of the fabric, wherein the fabric is configured to contact a body surface such that the zinc particles are in contact with a skin surface.

In certain embodiments, Applicants' method for treating hyperhidrosis comprises disposing onto a skin surface of a patient in need thereof a device including a fabric and a first metal disposed on the fabric. The fabric is configured to contact a body surface such that the zinc particles are in contact with a skin surface.

Figure 1:
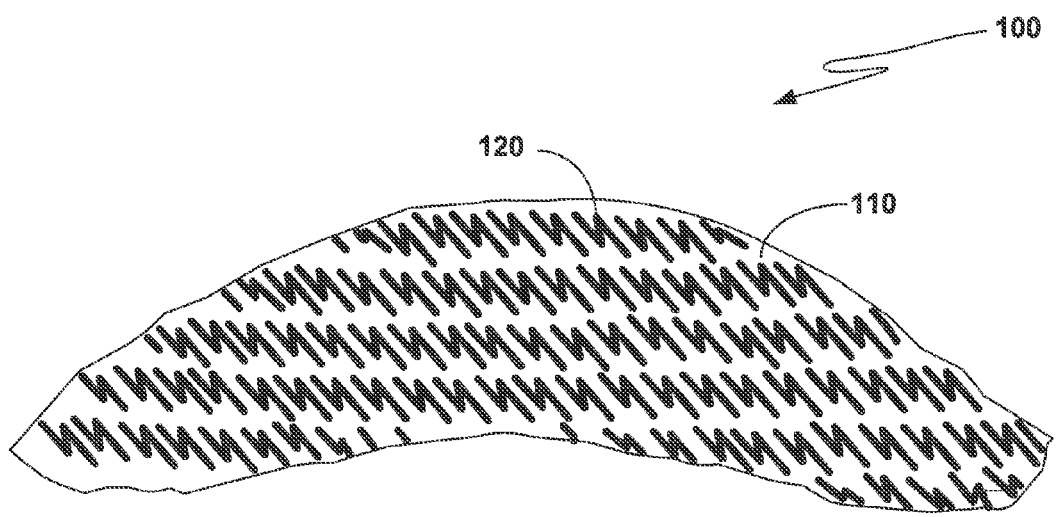
FIG. 1 illustrates an exemplary embodiment of Applicants' device for treatment of hyperhidrosis in the form an underbra insert including a pattern of metal deposition. As illustrated, this embodiment includes many discontinuous areas of metal deposition in which the overall fabric surface area is greater than the overall surface area of individual patterns of metal deposition.

Referring to FIG. 1, an embodiment of Applicants' device for treating hyperhidrosis is illustrated. As shown, Applicants' device comprises an underbra insert 100 that includes a fabric 110 and a plurality of metal deposition areas 120. The underbra insert 100 is worn inside a bra cup underneath the breast in contact with the skin as a bra underliner to treat excessive sweating associated with hyperhidrosis. As shown, the plurality of individual metal deposition areas 120 are discontinuous and uniformly distributed on the surface of the fabric 110 to cover a substantially consistent percentage of the surface area of the fabric 110. In certain embodiments, the metal deposition areas 120 cover from about 10% to about 90%. In other embodiments, the metal deposition areas 120 cover from about 20% to about 80%, from about 15% to about 75%, from about 25% to about 50%, or from about 30% to about 40% of the surface area of the fabric 110. Although FIG. 1 shows the plurality of metal deposition areas 120 substantially uniformly distributed on the surface of the fabric 110, in other embodiments, the plurality of metal deposition areas 120 may be randomly distributed on the surface of the fabric 110.

The underbra insert fabric 110, as illustrated in the embodiment of FIG. 1, comprises a single layer. However, in other embodiments, the fabric 110 may comprise one, two, or three or more layers of fabric including metal deposition areas on at least one surface of the device.

In certain embodiments, the fabric 110 comprises a woven textile, a non-woven textile, a fibrous mesh, anon-fibrous mesh, a textile mesh, a woven cloth, a non-woven cloth, or the like. In an embodiment, the fabric may comprise a polymeric film or a polymeric coating. In an embodiment, the fabric may be interwoven with elastic fibers, elastic bands, or metallic fibers. In certain embodiments, the fabric is electrically conductive or electrically non-conductive.

In certain embodiments, fabric 110 is permeable to ambient air. In certain embodiments, the plurality of individual metal deposition areas 120 comprise elemental zinc particles.

In an embodiment, the device includes a fastener configured to attach the device or the underbra insert 100 to the skin surface or to the surface of an article of clothing. For example, referring back to FIG. 1, in certain embodiments the surface of the fabric 110 comprises a surface of the fabric 110 including the plurality of metal deposition areas 120 in contact with the skin and an opposing surface of the fabric 110 in contact with an article of clothing. In certain embodiments, the opposing surface of the fabric 110 includes an adhesive configured to attach the fabric 110 to an article of clothing. For example, the underbra insert 100 as shown in FIG. 1 includes the plurality of metal deposition areas 120 on one surface of the fabric 110 configured for contact with the skin surface. An opposite surface of the underbra insert 100 (not shown) includes an adhesive or adhesive strips configured to adhere the underbra insert 100 to the interior of a bra surface. In an embodiment, the device is configured for attachment to an article of clothing via at least one of the group consisting of a VELCRO fastener, buttons, zippers, electrostatics, an adhesive, a hook and eye fastener, a thread, snaps, or the like.

In an embodiment, the surface of the fabric 110 including the plurality of metal deposition areas 120 further comprises an adhesive for attachment of the fabric to the skin surface. In an embodiment, the fabric of the device is flexible and/or conformable to the skin surface. In certain embodiments, the fabric of the device is compressive to the skin surface, for example and without limitation, a sock, a glove, a headband, or an elastic bandage.

In an embodiment, the fabric of the device comprises an article of clothing. For example, the fabric includes at least one member selected from the group consisting of a sock, a glove, a headband, a cap, a hat, a t-shirt, a bra, an underarm insert, pants, sleeves, underwear (undergarment clothing in contact with the skin). For example, FIGS. 2A and 2B illustrate exemplary embodiments of Applicants' device for treatment of hyperhidrosis in the form of socks including a plurality of continuous lines of metal deposition.

Figure 2A:
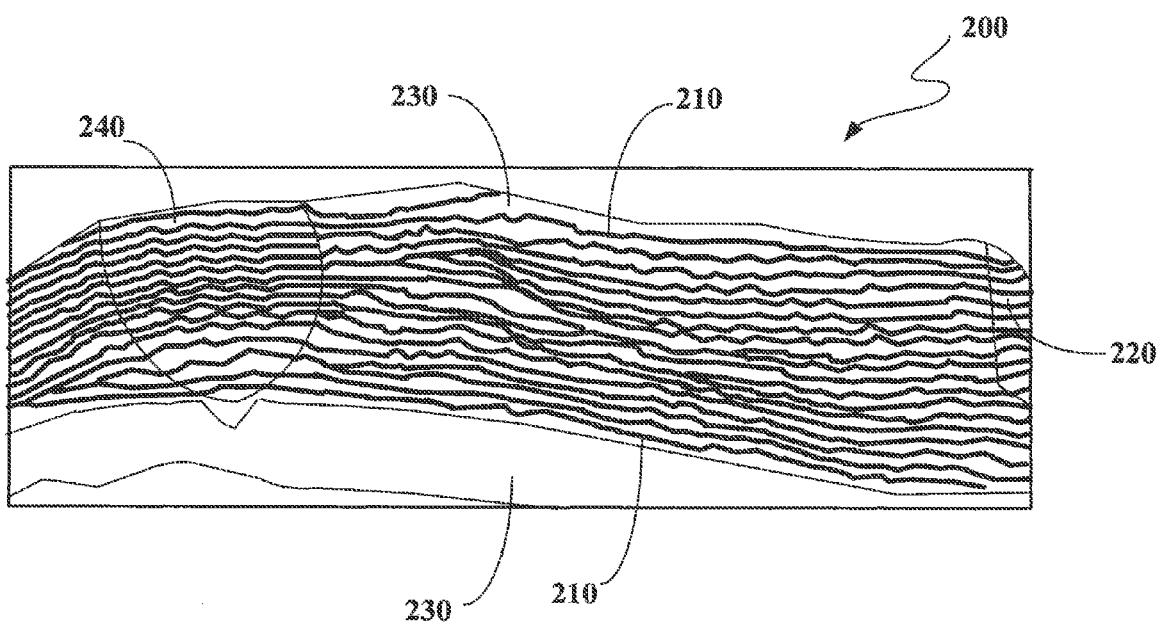
FIGS. 2A and 2B illustrate exemplary embodiments of Applicants' device for treatment of hyperhidrosis in the form of socks, each sock including a plurality of continuous lines of metal deposition.
Figure 2B:
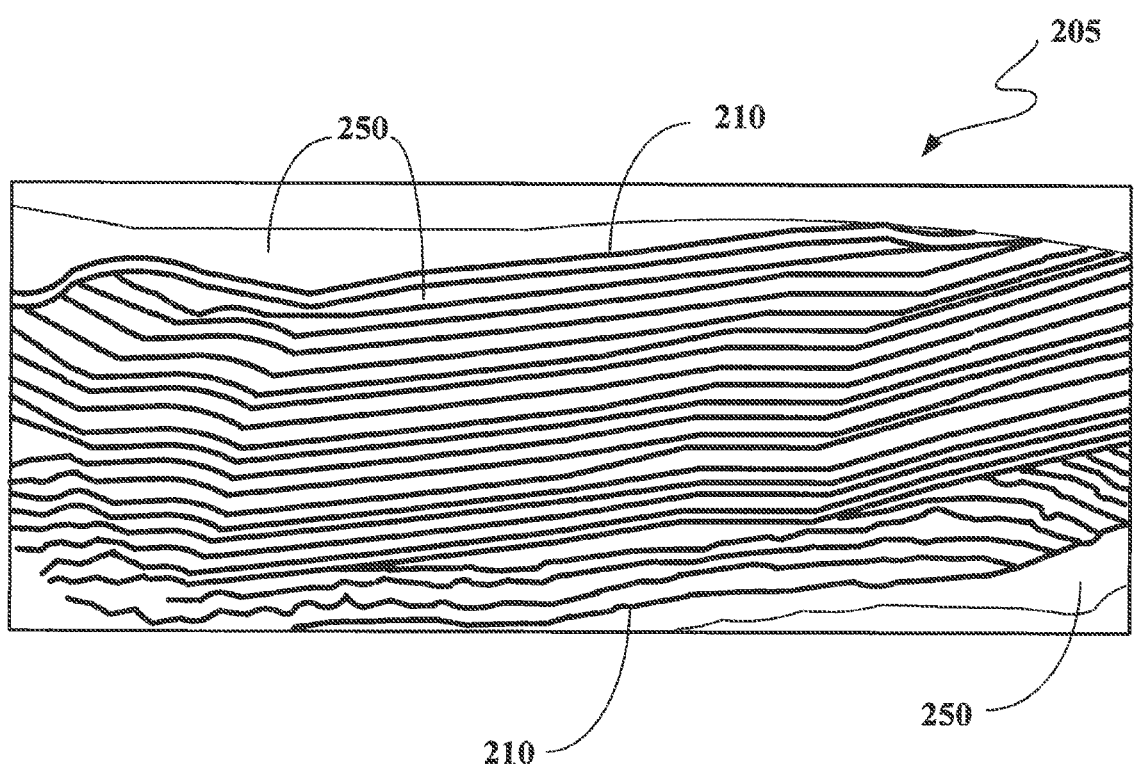

FIG. 2A illustrates sock 200 including a plurality of continuous lines of metal deposition 210, a reinforced fabric 220 of a toe region, a fabric 230 of a body of the sock 200, and a reinforced fabric 240 of a conforming heel of the sock 200. Similarly, FIG. 2B illustrates sock 205 also including a plurality of continuous lines of metal deposition 210, and a fabric 250 of the sock 205 body. As shown in FIG. 2B, the sock 205 comprises a heelless sock including a conforming single sock body void of reinforced toe and heel regions. The materials comprising fabrics 220, 230, 240, and 250 and the plurality of continuous lines of metal deposition 210 comprise any of the materials discussed herein regarding the fabric 110 and the plurality of metal deposition areas 120 of exemplary device underbra insert 100. FIGS. 2A and 2B illustrate the width of each line of the plurality of continuous lines of metal deposition 210 is less than the width of fabric 250 between each line of the plurality of continuous lines of metal deposition 210. However, in certain embodiments the width of each line of the plurality of continuous lines of metal deposition substantially equals the width of fabric between each line of the plurality of continuous lines of metal deposition. By "substantially equals," Applicant means within ± about 10% of the value of interest. In an embodiment, the width of each line of the plurality of continuous lines of metal deposition is greater than the width of fabric between each line of the plurality of continuous lines of metal deposition. In certain embodiments, the fabric 250 includes a ridged surface.

In certain embodiments, zinc is utilized as a powdered elemental crystal. In certain embodiments, the zinc utilized has a purity of about 99.99 percent. In certain embodiments, the zinc comprises a −325 mesh size. As those skilled in the art will appreciate, particles passing through a −325 mesh are considered the "fines."

In certain embodiments, the zinc particles are very uniform in size. In certain embodiments, the zinc particle size distribution is between about 4 microns to about 10 microns in diameter. These individual particle crystals approach the visible range and are easily seen as shiny crystals on the surface.

In certain embodiments, Applicants' socks comprise a woven fabric. In certain embodiments, Applicants' socks comprise a non-woven fabric. In certain embodiments, Applicants' socks comprise a braided fabric. In certain embodiments, Applicants' socks comprise a polymeric fabric. In certain embodiments, Applicants' socks are permeable to ambient oxygen.

In certain embodiments, Applicant applies a zinc coating to a body part, such as and without limitation, a foot using an immersion printing technique. Such a process is sometimes referred to as water transfer printing, water transfer imaging, or cubic printing.

In the process, a polyvinyl alcohol film is coated with a coating of zinc particles and is then floated on the surface of a vat of water. An activator chemical is sprayed on the film to dissolve it into a liquid and activate a bonding agent. A patient's foot is then lowered into the vat, through the floating zinc layer, which wraps around and adheres to it.

In certain embodiments, zinc particles are disposed on a tissue surface using a light tattoo.

In certain embodiments, Applicant utilizes a screen print method. A PVC silk screen ink is used as both as the vehicle and binder. Zinc particles are mixed into the ink and process it through the silk screens. The ink is heat cured under an oven to "set" the ink or make it solid. Since the zinc is a metal, this process does not affect the zinc, however, the ink is selected so to not encapsulate the zinc particles but leave them anchored to the fibers of the sock and exposed to the skin.

In certain embodiments, a plastisol ink is utilized in the screen printing process. Plastisol is a suspension of PVC particles in a liquid plasticizer. The suspension flows as a liquid. Zinc particles are mixed into the plastisol suspension, and that mixture is screen printed onto a fabric, such as and without limitation, a sock. In certain embodiments, the zinc/plastisol suspension is mixed with 20% Union stretch ink prior to application to the fabric.

When the coated fabric is heated to around 177 degrees Celsius, the plastic and plasticizer mutually dissolve each other. On cooling the mold below 60 degrees C., a flexible, permanently plasticized zinc coating is disposed onto the fabric.

In certain embodiments, a method for treating hyperhidrosis includes disposing onto a skin surface a device including a fabric having elemental zinc particles disposed thereon. The fabric is configured to contact the skin and to generate an electric current and metal ions when oxidized by ambient oxygen. The generation of such an electric current results in reducing the amount of sweat disposed on the skin surface thereby providing a treatment for hyperhidrosis.

In certain embodiments, Applicants' method for treating hyperhidrosis includes generating an electric current on the skin surface resulting in a reduction of an amount of sweat released by the skin. For example, in a non-limiting embodiment, the method includes contacting a skin surface with elemental zinc particles disposed on at least a portion of the fabric or flexible substrate.

The chemistry of Zinc-air batteries is instructive. Such batteries are powered by oxidizing zinc with oxygen from the air. During discharge, zinc particles form a porous anode, which is saturated with an electrolyte, namely sweat. Oxygen from the air reacts at the cathode and forms hydroxyl ions which migrate into the zinc paste and form zincate ($Zn(OH)_2$), releasing electrons to travel to the cathode.

The chemical equations for the zinc-air battery formed using Applicants' zinc-coated socks and ambient oxygen include:

$$\text{Anode: } Zn + 4OH^- \rightarrow Zn(OH)_4^{2-} + 2e^- \; (E_0 = -1.25 \text{ V}).$$

$$\text{Fluid: } Zn(OH)_4^{2-} \rightarrow ZnO + H_2O + 2OH^-$$

$$\text{Cathode: } 1/2 O_2 + H_2O + 2e^- \rightarrow 2OH^- \; (E_0 = 0.34 \text{ V})$$

Overall, the zinc oxygen redox chemistry recited immediately hereinabove comprises an overall standard electrode potential of about 1.59 Volts.

The is a gas exchange at the skin surface with a partial pressure of oxygen. The oxygen at the skin surface is a product of ambient oxygen in addition to oxygen diffusion from capillary blood flow. In certain embodiments, the zinc in contact with a patient's skin resulting from wearing, for example, my zinc-containing socks, in combination with sweat and transcutaneous oxygen complete the galvanic circuit described hereinabove.

The chemistry utilized by Applicants' zinc-coated socks differs from a more conventional galvanic cell. As those skilled in the art will appreciate, a galvanic cell, or voltaic cell, named after Luigi Galvani, or Alessandro Volta respectively, is an electrochemical cell that derives electrical energy from spontaneous redox reactions taking place within the cell. It generally consists of two different metals connected by a salt bridge, or individual half-cells separated by a porous membrane. In contrast, the chemistry of Applicants' zinc-air battery does not require use of a second metal. Applicants' method to treat hyperhidrosis utilizes elemental zinc particles disposed onto a fabric, where the elemental zinc particles are in contact with the skin. In certain embodiments, other than elemental zinc metal and zinc oxides formed therefrom, no other or additional metals or metal oxides are needed or are utilized in Applicants' method and device.

The method described herein may include any of the fabric and metal materials previously described with respect to the exemplary device described herein (i.e., the underbra insert 100 or socks 200 and 205).

The following Example is presented to further illustrate to persons skilled in the art how to make and use the invention. This Examples is not intended as a limitation, however, upon the scope of the invention, which is defined by claims recited hereinbelow.

Example I

During the initial interview, study participants received protocol instructions and rated their sweating severity utilizing the standardized "Hyperhidrosis Disease Severity Scale" questionnaire. All participants rated their sweating severity as either a 2 (tolerable but sometimes interferes with daily activities) or a 3 (barely tolerable and frequently interferes with daily activities).

Participants were provided with 4 pairs of socks with only the right foot (clearly marked) treated with the zinc ions. They were asked to wear them as much as possible over a 21 day period and keep a wear record on a time grid. At the point they noticed a decrease in sweating of the right foot, they were asked to mark the time grid in red.

Participants reported wearing the socks from 14 to 24 hours each day. A decrease in sweating was noted in all participants, irrespective of gender and age, and persisted throughout the study period. Average time to note a relief in sweating symptoms was 9 days—the earliest noted on day 5 and the latest on day 13.

Preliminary results indicate that frequent exposure of sweating feet to the low current created by the zinc-containing socks resulted in a significant decrease in sweating that persisted once relief of symptoms became apparent to the participant.

Exit survey indicated that patients found the right sock to be comfortable and the right foot to have less sweating and odor. They would like to have pairs with both socks treated, and would like to try other zinc-containing Sportswear clothing. They would recommend the zinc-containing socks to others and would purchase them if available.

While the preferred embodiments of the present invention have been illustrated in detail, it should be apparent that modifications and adaptations to those embodiments may occur to one skilled in the art without departing from the scope of the present invention as set forth herein.

We claim:

1. A method for treating hyperhidrosis comprising disposing onto a skin surface of a patient in need thereof a device comprising:
    a fabric;
    elemental zinc particles printed onto one surface of the fabric as a plurality of lines, wherein
    the fabric is configured such that said elemental zinc particles contact a skin surface when worn by a patient; and
    a width of each line of the plurality of lines of said elemental zinc particles is less than a width of fabric between each lines of the plurality of lines of said elemental zinc particles, wherein said fabric in contact with the skin generates an electric current and metal ions when oxidized by ambient oxygen, forming an air-zinc battery.

2. The method of claim 1, comprising attaching the fabric to the skin surface.

3. The method of claim 1, further comprising reducing an amount of sweat disposed on said skin surface.

4. The method of claim 1, wherein the device does not comprise a second metal or a second metal oxide.

5. The method of claim 1, wherein the fabric comprises an article of clothing.

6. A method for treating hyperhidrosis comprising:
    contacting a skin surface with elemental zinc particles printed as a plurality of lines onto one surface of a flexible substrate;
    oxidizing the elemental zinc particles whereby to generate an electrical current and metal ions forming an air-zinc battery which reduces an amount of sweat disposed on the skin surface contacted by the flexible substrate.

7. The method of claim 6, wherein contacting the skin surface with a first metal does not comprise contacting the skin surface with a second metal or a second metal oxide.

8. The method of claim 6, further comprising: mixing said elemental zinc particles into a screen printing ink; printing the screen printing ink/elemental zinc particle mixture onto said fabric; and heating said fabric to about 177° C. to form a plasticized zinc coating on said fabric.

9. The method of claim 8, further comprising disposing onto said skin surface said fabric comprising said plasticized zinc coating.

10. The method of claim 9, wherein said oxidizing is performed by ambient oxygen.

11. A method to reduce sweating of a person comprising:
    providing a fabric having elemental zinc particles printed onto one surface of the fabric as a plurality of lines, wherein a width of each line of the plurality of lines of said elemental zinc particles is less than a width of fabric between each line of the plurality of lines of said elemental zinc particles, and disposing the fabric in contact with a skin surface of the person such that said elemental zinc particles contact the person's skin surface, wherein said fabric in contact with the skin generates an electric current and metal ions when oxidized by ambient oxygen, forming an air-zinc battery.

12. The method of claim 11, further comprising attaching the fabric to the skin surface.

13. The method of claim 11, wherein the fabric does not comprise a second metal or a second metal oxide.

14. The method of claim 11, wherein the fabric comprises an article of clothing.

15. The method of claim 11, wherein said fabric is provided by mixing elemental zinc particles into a screen printing ink; printing the screen printing ink/elemental zinc particle mixture onto said fabric; and heating said fabric to about 177° C. to form a plasticized zinc coating on said fabric.

16. The method of claim 15, wherein said fabric comprising said plasticized zinc coating is disposed in contact with said skin.

17. The method of claim 16, wherein said oxidizing is performed by ambient oxygen.

* * * * *